(12) United States Patent
Bombardelli et al.

(10) Patent No.: US 6,514,732 B1
(45) Date of Patent: Feb. 4, 2003

(54) PROCESS FOR PREPARING BACCATIN

(75) Inventors: Ezio Bombardelli, Milan (IT); Birgitta Menhard, Monheim (DE); Meinhart Hans Zenk, München (DE)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 09/582,223

(22) PCT Filed: Jan. 29, 1999

(86) PCT No.: PCT/EP99/00599

§ 371 (c)(1),
(2), (4) Date: Jul. 20, 2000

(87) PCT Pub. No.: WO99/40216

PCT Pub. Date: Aug. 12, 1999

(30) Foreign Application Priority Data

Feb. 6, 1998 (DE) ......................................... 198 04 815

(51) Int. Cl.⁷ ................................................ C12P 17/02
(52) U.S. Cl. ....................................... 435/123; 435/193

(58) Field of Search ................................... 435/193, 123

(56) References Cited

PUBLICATIONS

Chemical Abstracts, vol. 130, Abstract No. 207279.
Chemical Abstracts, vol. 130, Abstract No. 110419.
Chemical Abstracts, vol. 124, Abstract No. 7137.
Nanduri et al., Biotechnol, Bioeng., (1995) 48(5), 547–550.*

* cited by examiner

*Primary Examiner*—Irene Marx
(74) *Attorney, Agent, or Firm*—Arent Fox Kintner Plotkin & Kahn, PLLC

(57) ABSTRACT

A process for preparing baccatin and/or baccatin derivatives is described in which 10-deacetylbaccatin or a 10-deacetylbaccatin derivative is reacted in the presence of an isolated enzyme and an acetyl donor, the enzyme used being an acetyl transferase having a molecular weight of from 70 to 72 kD, determined by SDS-PAGE, which acetyl transferase is obtainable from *Taxus chinensis* cell cultures.

13 Claims, No Drawings

PROCESS FOR PREPARING BACCATIN

The invention relates to a process for preparing baccatin or baccatin derivatives by selective acetylation of the corresponding 10-deacetyl compounds, to an isolated enzyme which catalyses this acetylation reaction and to a process for preparing the enzyme.

Taxol is a promising agent for treating cancer which has antileukaemic and tumour-inhibiting activity (see, for example: M. Suffnes et al., in "The Alkaloids, Chemistry and Pharmacology", A. Brossi, Ed., Academic Press: Orlando, Fla., 1985, Vol. XXV, Chapter 1). Originally, taxol was obtained from the bark of certain yew trees (*Taxus taxaceae*). However, the isolation of taxol from bark is difficult and expensive, and the desired taxol is obtained from the bark in only very poor yields (40 to 165 mg/kg) (see, for example, R. W. Miller et al., J. Org. Chem. 46 (1981) 1469–1474; V. Sénilh et al., J. Nat. Procl. 47 (1984) 131–137; N. Magri et al., J. Org. Chem. 51 (1986) 797–802). Moreover, the use of bark causes the yew trees, which grow back very slowly, to die, so that there are only limited supplies of starting materials.

Since the discovery of the properties of taxol which recommend it for use as a chemotherapeutic agent for cancer, numerous efforts have been made to prepare the compound by synthetic or semi-synthetic processes. Thus, it has been attempted to prepare the taxol structure by organic synthesis (see, for example, W. F. Berkowitz et al., J. Org. Chem. 52 (1987) 1119–1124). However, because of the complexity of the molecule, it has hitherto not been possible to prepare taxol in practically useful amounts by total organic synthesis.

A further route which was used to obtain taxol is partial synthesis starting from a precursor which is easily obtainable in large amounts. One of these routes starts with 10-deacetylbaccatin-III which can be extracted easily and in large amounts from the leaves of *Taxus baccata* L (G. Chauviere et al., Seances Acad. Sci., Ser. 2, 1981, 293, 501–503). Here, it is possible to isolate approximately 1 g of 10-deacetylbaccatin III per kilogram of leaves, the leaves growing back rapidly. Thus, it is possible without any problems to obtain large amounts of the precursor 10-deacetylbaccatin III.

The desired active compound taxol can be prepared from this precursor, obtained from biological material, by partial synthesis. However, it has been found that, as similar as the structures of 10-deacetylbaccatin III and taxol may be, this partial synthesis still entails significant problems and can for the most part be carried out successfully only by using specific protective groups, giving the desired product taxol in only poor yields.

Denis et al., (J. Am. Chem. Soc. 110 (1988), 5917–5919) describe the synthesis of 10-deacetylbaccatin III to give taxol in two steps. In the first step, 10-deacetylbaccatin III is acetylated chemically in the 10-position. In the second step, baccatin is converted into taxol. However, the first step is not regiospecific, so that acetylation of 10-deacetylbaccatin also occurs, in particular, in position 7. Because of this it is necessary to block the hydroxyl group at this position against acetylation by using a protective group. Exclusive acetylation in the 10-position could only be achieved by using a protective group. However, the use of a protective group entails two more process steps (introduction and removal of the protective group) which is, on the one hand, expensive and, on the other hand, considerably reduces the yield of the product obtained. A further disadvantage of using protective groups consists in the fact that, in particular when the product is used as a pharmaceutical active compound, complicated purification and analysis processes have to be carried out subsequently in order to ensure that there are no more molecules which still carry protective groups present in the product.

Zocher et al. (Biochem. Biophys. Res. Commun., 229 (1996), 16–20) describe a taxol biosynthesis. Here, in an intermediate step, the acetylation of 10-deacetylbaccatin III to give baccatin III was carried out with the aid of crude plant extracts from the roots of *Taxus baccata*. However, it was not possible to isolate or characterize substances which effect the acetylation. A disadvantage of using a crude extract is the fact that numerous other reactions, in particular acetylation at other positions, can also be initiated or influenced by substances present in the crude extract. Moreover, a crude plant extract has no defined and reproducible composition, so that the use of crude plant extracts results in uncontrollable and varying reactions and yields.

It was therefore an object of the present invention to provide a process for preparing baccatin and baccatin-like baccatin derivatives by selective acetylation of the corresponding 10-deacetyl compounds in position 10. It was a further object to provide an isolated substance which specifically catalyses this reaction.

According to the invention, these objects are achieved by a process for preparing baccatin or baccatin derivatives which is characterized in that 10-deacetylbaccatin or a 10-deacetylbaccatin derivative is reacted in the presence of an isolated enzyme and an acetyl donor, the enzyme being an acetyl transferase having a molecular weight of from 70 to 72 kD, determined by SDS-PAGE (sodium dodecylsulfate polyacrylamide gel electrophoresis, which acetyl transferase is obtainable from *Taxus chinensis* cell cultures. It has been found that regioselective acetylation in position 10 is catalysed by an isolated enzyme which can be obtained from suspended *Taxus chinensis* cell cultures. Surprisingly, it has been found that using the isolated and purified enzyme, it is possible to achieve high regiospecificity with respect to the acetylation in position 10. This specificity is preferably >80%, more preferably >90% and most preferably >95%. It has been found that using the enzyme used according to the invention, it is possible to achieve a specificity of >99%. Here, a specificity of >80% means that acetylation has taken place to more than 80% in position 10 and to less than 20% in other positions of the starting material. Consequently, other hydroxyl groups which are present in the starting material do not have to be blocked with a protective group, since acetylation of these other hydroxyl groups occurs to only a very limited extent, if at all, when the enzyme according to the invention is used.

Surprisingly, it has been found that the enzyme used according to the invention has a high substrate specificity. Thus, only 10-deacetylbaccatin or 10-deacetylbaccatin derivatives which have a 10-deacetylbaccatin III-like configuration at and in the vicinity of the C10-position are converted. In particular, baccatin derivatives where the access to position 10 is blocked by voluminous substituents, such as, for example, 10-deacetyltaxol and 10-deacetylcephalomannin, are not acetylated. A precondition for baccatin derivatives to be recognized as substrates by the enzyme according to the invention is therefore that these derivatives, which have a taxane ring structure, essentially correspond to 10-deacetylbaccatin III in positions 7, 8, 9, 10, 11, 12 and 13, i.e. that they do not carry any other substituents in these positions or only substituents having a small volume. The process is preferably suitable for baccatin derivatives which carry the same substituents as 10-deacetylbaccatin III in positions 7 to 13, or carry at least some substituents having a smaller volume than the substituents of 10-deacetylbaccatin III, in particular hydrogen. Voluminous substituents in the other positions do not interfere with the reaction. The process is particularly preferably employed for acetylating 10-deacetylbaccatin III. Furthermore, the process is particularly preferably used for selectively acetylating 14-hydroxy-10-deacetylbaccatin III in position 10.

In contrast, 10-deacetylbaccatin III derivatives whose hydroxyl group in position 7 is blocked by a voluminous protective group, such as, for example, 7-TES-10-DAB III or 7-BOC-10-DAB III, are not recognized as substrates by the enzyme according to the invention. However, such a blocking is not required, since regioselective acetylation in position 10 takes place even when other hydroxyl groups are present in other positions.

Using the process according to the invention, it is possible to acetylate taxane derivatives, which have the same, fewer or less voluminous substituents in positions 7 to 13 than 10-deacetylbaccatin III, selectively in position 10. Such taxane derivatives in which the substituents which are present in 10-deacetylbaccatin III (i.e. OH in position 7, $CH_3$ in position 8, =O in position 9, OH in position 10, $CH_3$ in position 12 and OH in position 13) are present or are replaced by a radical which is smaller or has the same volume, in particular by hydrogen, are included here under the term 10-deacetylbaccatin derivatives, and can likewise be acetylated regiospecifically, if they have an OH group in position 10. Examples of such derivatives are 10-deacetyltaxuyunnanin C, 10,14-deacetyltaxuyunnanin C, 2,10,14-deacetyltaxuyunnanin C, 5,10,14-deacetyltaxuyunnanin C and 2,5,10,14-deacetyltaxuyunnanin C.

The process according to the invention is carried out in the presence of an acetyl donor. Suitable acetyl donors are in principle any substances which donate an acetyl group in the catalytic conversion of the 10-deacetyl starting material. The reaction is preferably carried out in the presence of the acetyl donor acetyl coenzyme A.

From a technical point of view, the use according to the invention of an isolated enzyme offers many advantages. In particular with respect to the conversion rate and with respect to the reproducibility, the reaction can be controlled easily if an isolated enzyme is used.

The enzyme used preferably has an isoelectric point of from pH 5.4 to 5.8, preferably from 5.5 to 5.7 and in particular of pH 5.6. Furthermore, it has been found that the enzyme used according to the invention has a Michaelis constant $K_M$ for acetyl coenzyme A of from 55 to 65 $\mu$m, preferably of from 59 to 63 $\mu$M and in particular of 61 $\mu$M.

The invention furthermore provides an isolated enzyme which is characterized in that a) it acetylates 10-deacetylbaccatin III in the presence of an acetyl donor, in particular acetyl coenzyme A, selectively at position 10, b) has a molecular weight of from 70 to 72 kD, determined by SDS-PAGE and c) is obtainable from *Taxus chinensis* cell cultures.

The enzyme according to the invention is preferably present in a purity of >50%, in particular >80%, more preferably >90% and most preferably >95%. The enzyme according to the invention is distinguished by the fact that it acetylates 10-deacetylbaccatin III in the presence of an acetyl donor, in particular acetyl CoA, selectively in position 10. This means in particular that acetylation of the other hydroxyl groups of 10-deacetylbaccatin III in positions 1,7 and 13 is virtually not observed. The acetylation reaction has in particular a selectivity of >50% with respect to position 10, preferably >80%, more preferably >90% and most preferably >95%.

The isolated enzyme is furthermore characterized by a molecular weight of from 70 to 72 kD, determined by SDS-PAGE. To determine the molecular weight, 0.3 $\mu$g of homogeneous protein was chromatographed in a denaturizing 10% strength SDS gel in parallel with Marker proteins of a known molecular weight (Rainbow Marker). The proteins were made visible by silver staining, and the molecular weight was determined by comparing the Rf values of the calibration proteins and the enzyme according to the invention. The molecular weight which had been determined by SDS gel electrophoresis was confirmed by gel filtration using a suitable gel filtration column. The gel filtration was carried out using a biosilect-SEC 250-5 column (Biorad) which had been equilibrated using 50 mM tris, pH 8.5, 20 mM 2-mercaptoethanol, in an FPLC unit (Biologic Workstation, Biorad), using a flow rate of 0.2 ml/min. The column was initially calibrated using proteins of a known molecular weight. Under identical conditions, 50 $\mu$g of the protein according to the invention were then passed through the column. 250 $\mu$l fractions of the eluate were collected, and the activity of the eluate was determined as described below. The molecular weight was determined by comparing the elution times with the known standards.

The enzyme according to the invention can be isolated from cell cultures of *Taxus chinensis*. It has an isoelectric point of from pH 5.4 to 5.8, preferably from pH 5.5 to 5.7 and in particular of pH 5.6. Furthermore, the Michaelis Menten constant $K_M$ found for the enzyme used was from 55 to 65 $\mu$M, preferably from 59 to 63 $\mu$M and in particular 61 $\mu$M for acetyl coenzyme A.

The enzyme according to the invention is an acetyl transferase, in particular an acetyl CoA 10-hydroxytaxane-O-acetyl transferase.

The invention furthermore provides a process for preparing the enzyme described above, which is characterized in that the enzyme is isolated from an enzyme-containing source by using known purification processes and after each purification the fractions in which the enzyme is present are determined by adding 10-deacetylbaccatin or a 10-deacetylbaccatin derivative and an acetyl donor, and the acetylation product formed is detected.

The enzyme-containing source used can be, for example, a plant extract. The enzyme-containing source used is preferably a cell culture, in particular a suspended cell culture. The use of a cell culture is advantageous since it allows large amounts of starting material to be obtained. Compared to using a crude extract as enzyme-containing source, when using a cell culture, it is possible to purify the enzyme to a high degree of purity owing to the large amount of starting material. Particular preference is given to using a starting material originating from *Taxus chinensis*, for example a *Taxus chinensis* cell culture.

To purify the enzyme from the starting material, it is possible to employ known purification processes for the isolation of enzymes or proteins. Processes which are preferably used include the ammonium sulphate precipitation from the crude extract, and also chromatographic purification processes, such as, for example, the use of a Sephadex G-25 column, anion exchange chromatography, for example over DEAE-Sephacel, gel filtration, for example over Ultrogel AcA 44, anion exchange chromatography, for example over HighQ, chromatography over a hydroxyapatite column, dye affinity chromatography, for example over High Trap Blue, hydrophobic interaction chromatography, for example over phenyl sepharose and/or dye affinity chromatography, for example over Mimetic Green 1A6XL. Purification preferably includes at least one step in which anion exchange chromatography over HighQ is employed. The HighQ column is an anion exchanger having —$N^+(CH_3)_3$ groups as ligands. It has been found that in particular in this purification step, substances are removed which catalyse acetylation at positions other than position 10.

In the process according to the invention, the enzyme activity of the fractions is determined after each purification step to determine which fractions contain the enzyme. To this end, the fraction or an aliquot of the fraction is admixed with 10-deacetylbaccatin or a 10-deacetylbaccatin derivative, as defined above, and an acetyl donor. In the fractions in which the desired enzyme is present, product which is acetylated in position 10 can be detected. Preference is given to using 10-deacetylbaccatin III or 10-deacetyltaxuyunnanin C for this test. The acetylation product formed can be detected by using suitable marker groups in the starting materials. Preference is given to using a labelled acetyl donor. Such a labelled acetyl donor comprises a labelled acetyl group which can then be used to determine product which has been acetylated in position 10. Preference is given to using a radioactively labelled acetyl donor. Here, suitable radioactive marker groups are $^{13}C$ and $^{14}C$. The acetyl donor used is particularly preferably an acetyl coenzyme A, in particular [$2$-$^{14}C$]-acetyl coenzyme A.

It is also possible to carry out the detection using labelling with a heavy isotope. In this case, the reaction product can be determined by mass spectrometry.

Using the process according to the invention for preparing baccatin or baccatin derivatives employing the enzyme according to the invention, it is possible to prepare baccatin or taxane compounds which have been specifically acetylated in the 10-position. Such compounds are of interest in particular as starting materials for the partial synthesis of taxol. Accordingly, the invention also provides a process for preparing taxol and/or taxol derivatives which is characterized in that baccatin or baccatin derivatives prepared by the process described above are reacted by known processes to give taxol or taxol derivatives. The partial conversion of baccatin or baccatin derivatives to give taxol or taxol derivatives is described in the prior art and entails essentially the introduction of suitable substituents at the hydroxyl group in position 13 of the baccatin derivatives. The baccatin derivatives which are suitable for this purpose consequently have a free OH group at least in position 13.

The reaction of baccatin derivatives to give taxol or taxol derivatives is carried out in particular by esterifying the OH group in position 13 of the baccatin derivatives with a suitable acid. Such processes are described in detail in the literature, for example in U.S. Pat. No. 4,814,470 (Colin et al.,), in U.S. Pat. No. Re. 34,277 (Denis et al.), in EP 0,400,971 A2, in U.S. Pat. No. 4,924,011 (Denis et al.), in U.S. Pat. No. 5,476,954 (Bourzat et al.) and in Denis et al., J. Am. Chem. Soc. 110 (1988), 5917–5919.

The invention is illustrated in more detail by the examples below.

EXAMPLE 1
Cultivation of *Taxus chinensis* Cell Suspensions

The *Taxus chinensis* suspension cultures used were from the collection of the Institute for Pharmaceutical Biology of the University of Munich, and they originated from the needles of a *T. chinensis* tree. The cultures were allowed to grow at 24° C., 100 rpm and 1500 lux for 14 days. Using a sterile 50 ml pipette, 150 ml of cell suspension were then transferred into 250 ml of B5+1 medium:

Composition of the B5+1 medium (modified according to Gamborg, Miller, Ojima: Experimental Research, 1968, 50, pp. 151–158).

| | |
|---|---|
| Naphthylacetic acid | 10 $\mu M$ |
| Benzylaminopurine | 0.2 $\mu M$ |
| | mg/l |
| $NaH_2PO_4.H_2O$ | 150 |
| $CaCl_2.2H_2O$ | 150 |
| $(NH_4)_2SO_4$ | 134 |
| $MgSO_4.7H_2O$ | 250 |
| $KNO_3$ | 2500 |
| $FeSO_4.7H_2O$ | 25.6 |
| $Na_2EDTA.2H_2O$ | 34.27 |
| KJ | 0.75 |
| $MnSO_4.H_2O$ | 10 |
| $H_3BO_3$ | 3 |
| $ZnSO_4.7H_2O$ | 3 |
| $Na_2MoO_4.2H_2O$ | 0.25 |
| $CuSO_4.5H_2O$ | 0.25 |
| $CoCl_2.6H_2O$ | 0.25 |
| Nicotinic acid | 1 |
| Thiaminium dichloride | 10 |
| Pyridoxol hydrochloride | 1 |
| meso-Inositol | 1000 |
| D-(+)-sucrose | 20,000 |
| pH | 5.6 |
| NZ amines | 1000 |

The NZ amines were added to the medium as a sterile stock solution (10 g/l) under sterile conditions after autoclaving and cooling.

On the third day after this inoculation, 30 $\mu M$ of methyl jasmonate (from Serva) were added, and the culture was allowed to grow for another 4 days (Gundlach, H., Müller, M. J., Kutchan, T. M., Zenk, M. H., 1992, Proc. Natl. Acad. Sci. USA, 89, p. 2389–2393). The cells were then separated from the medium by vacuum filtration and, after shock freezing with liquid nitrogen, used for the enzyme maceration. However, it was also possible to store the cells at −20° C. for up to one month; after this, the activity of the desired enzyme decreased considerably.

EXAMPLE 2
Enzyme Test for the Determination of the Acetyltransferase Activity To be able to purify, characterize and detect an enzyme, it is essential that precise, sufficiently sensitive test methods are available. In this case, it was the detection of the product formed, for example of taxuyunnanin C from 10-deacetyltaxuyunnanin, and a simple and reliable method was developed for this purpose.

A sufficient amount of the enzyme solution to be tested was pipetted into 50 $\mu l$ of tris buffer (0.8 M, pH 8.5) in an Eppendorf cap. 30 $\mu l$ of purified acetyl CoA (5 nmol of unlabelled and 0.02 $\mu Ci$-[$2$-$^{14}C$]acetyl coenzyme A) and 15 nmol of a 3 mM stock solution of 10-deacetyltaxuyunnanin C dissolved in DMSO were then added (for the control only the corresponding amount of DMSO instead of this taxane). The mixture was incubated at 35° C. for 30 minutes and then acidified using 20 $\mu l$ of 12% $H_2SO_4$, the taxuyunnanin C formed was extracted using 600 $\mu l$ of tert-butyl methyl ether (10 min. in an overhead shaker) and the mixture was then centrifuged (4 min at 14,000 rpm in an Eppendorf centrifuge). The unreacted [$2$-$^{14}C$]acetyl CoA which was still present remained in the aqueous phase. 500 $\mu l$ of the organic phase were evaporated to dryness in a stream of air, which simultaneously removed any [$2$-$^{14}C$]acetic acid present which, owing to the earlier acidification, was present as the acid and was therefore volatile. Using a scintillation counter (Multipurpose Scintillation Counter LS 6500, from Beckmann) or a thin-layer radioscanner (Automatic TLC Linear Analyser, from Berthold), the type and the amount of the product formed were determined. The former apparatus was used to determine the conversion and thus the activity of the enzyme using the cpm values counted. With the aid of thin-layer chromatography (TLC) (mobile phase: chloroform:acetonitrile 7:3) and the subsequent evaluation using a radioscanner, it was possible to check whether the radioactivity measured using the scintillation counter did indeed correspond to a peak in the region of the Rf value of the expected product.

EXAMPLE 3
Purification of the Acetyl Transferase
3.1. Tissue Maceration and Desalting via Sephadex G25

To obtain the crude protein extract, 7 day-old suspension cultures were used which had been elicited with 30 µM of methyl jasonate on the third day after inoculation. 200 g of cells which had been freshly filtered off with suction were shock-frozen using liquid nitrogen. In an ice-cooled mortar, these cells were then mixed with 20 g of PVPP, and thawed with stirring using 400 ml of standard buffer A (100 mM of boric acid/NaOH, pH 8.5, 20% of glycerol, 20 mM of 2-mercaptoethanol. The PVPP binds some of the phenols, inter alia the tanning agents which are present in the extract, which interfere with the further purification process. The homogeneous cell pulp was then filtered through 4 layers of mull, and the press-juice was centrifuged at 15,000×g (10 min, SS34 rotor).

The ice-cooled supernatant was mixed with 50 ml of calcium phosphate gel which had been suspended in standard buffer A (100 mM boric acid/NaOH, pH 8.5, 20% glycerol, 20 mM 2-mercaptoethanol). The amount by volume is the amount of gel which is obtained after 10 minutes of centrifugation at 2500 rpm and corresponds to 1.9 g of $Ca_3(PO_4)_2$ (dry weight). This mixture was allowed to stand in the ice-bath with occasional stirring for 10 minutes. During this time, the accompanying substances such as, for example, the tanning agents which are present in large amounts, should be adsorbed onto the gel. The acetyl transferase remained in solution and was separated from the gel material by subsequent centrifugation (6000×g, 5 min., GSA rotor).

The gel pellet was subsequently once more taken up in 75 ml of standard buffer A, stirred with a glass rod for 5 minutes and centrifuged at 6000 rpm (GSA rotor) for another 5 minutes since some of the acetyl transferase had been adsorbed onto the gel and was released into the supernatant by this aftertreatment. If no calcium phosphate gel was employed, major difficulties were encountered in the further purification process, since the accompanying substances which were still present in this case rapidly blocked the membrane of the mixer cell, and the colour of the columns that were subsequently used changed to a dark brown and their binding capacities were rapidly reduced.

With slow stirring, the combined ice-cooled supernatant was admixed a little at a time with ammonium sulphate until 70% saturation had been reached, and slow stirring was continued for another 30 min. after the addition was complete. The precipitated protein could subsequently be pelleted at 15,000 rpm (10 min., SS34 rotor). The precipitate was carefully resuspended in 30 ml of standard buffer B (50 mM tris/HCl, pH 8.5, 20% glycerol, 20 mM 2-mercaptoethanol) and the solution was desalted using this buffer and a Sephadex G25 column (Pharmacia: 2.7 cm φ×7 cm), and at the same time, 60% of the foreign protein were separated off.

[G25 eluate: 82 ml, 78 mg of protein]
3.2. Anion Exchange Chromatography Over DEAE Sephacel DEAE Sephacel is a modified cellulose to which positively charged diethylaminoethyl radicals are attached. If the isoelectric point of dissolved proteins is more acidic than the buffer used, they are present as anions and can therefore bind to the positively charged column material. The addition of stronger anions, such as, for example, $Cl^-$ or $SO_4^{2-}$, reduces the electrostatic interaction of adsorbed protein and DEAE groups. Consequently, the protein anions are exchanged for the inorganic anions and the enzyme is thus eluted.

In this purification step, 24.4% of the foreign protein were removed, and also, in particular, accompanying substances, inter alia phenol-containing tanning agents. Even during the first use, the colour of the column material changed to a dark brown, but it was possible to purify it substantially using 1 M NaOH. This step considerably reduced the soiling of the columns used later on in the purification process.

The initial flowthrough of the DEAE column (2.5 cm φ×5 cm), including 30 ml of standard buffer B (50 mM Tris/HCl, pH 8.5, 20% of glycerol, 20 mM of 2-mercaptoethanol) which were used to wash the column, were concentrated by pressure filtration in a mixer cell (Amicon, 400 ml, membrane PM 10) to a volume of 5 ml.
[DEAE eluate: 110 ml, 59 mg of protein]
3.3 Gel Filtration Over Ultrogel AcA 44

The principle of gel filtration is based on the fact that macromolecules, such as, for example, proteins, are distributed between a matrix having a defined pore size (exclusion of volume) and the surrounding liquid depending on their size and form. Molecules which are too big to be able to penetrate into the pores of the gel pass the particles and are consequently eluted more rapidly than medium-sized proteins which are initially delayed by the pores, but without penetrating into them. Even smaller molecules, inter alia salt ions, initially enter the pores, and they only leave them after a certain residence time, owing to which they remain on the column the longest.

This technique is very gentle since there are virtually no interactions between material and protein, and there is no need to use special buffers.

Moreover, the eluate is completely desalted, since the smaller ions, in this case sulphate ions, remain on the column much longer than the active protein.

The gel used was a polyacrylamide agarose gel which is suitable for a fractionation range of 10–130 kD (Ultrogel AcA 44, from Serva).

The concentrated protein solution was separated overnight using a column (2.8 cm φ×100 cm) which had been equilibrated with standard buffer B at a flow rate of 20 ml/h. The 60 fractions (6.5 ml each) were tested for protein content and acetyl transferase activity. The fractions showing the main activity were combined and purified further.

Using this eluate, it was possible to measure the specific activity of the acetyl transferase. In addition to distinct peaks at low Rf values, the thin-layer chromatogram also showed a peak at the height of the Rf value of taxuyunnanine. [AcA eluate: 53 ml, 25.7 mg, the total activity of 724 pcat was taken to be 100%]. By means of this gel filtration, 57% of the foreign protein were separated off.
3.4 Anion Exchange Chromatography Over HighQ Like the DEAE column, the HighQ column, which has $-N^+(CH_3)_3$ groups as ligands, is also an anion exchanger, but in contrast to the former a strong anion exchanger, i.e. its state of ionization does not change over a wide pH range. The degree of dissociation and consequently the exchange capacity of weak exchangers varies considerably at different pH values. Since the HighQ column material consists of densely packed resin particles having a size of approximately 10 μm, there is a high counterpressure, so that the column has to be operated using an FPLC unit (from Biorad).

The salt-free AcA eluate (53 ml) was pumped onto the HighQ 5 ml ready-made-up column, which had been equilibrated with standard buffer B (50 mM tris/HCl, pH 8.5, 20% glycerol, 20 mM 2-mercaptoethanol) using a flow rate of 2 ml/min, and the column was washed with the same buffer. The colourless initial flowthrough already contained part of the inactive protein, and further foreign protein and yellow accompanying substances were removed using 0.07 M KCl in standard buffer B (50 mM tris/HCl, pH 8.5, 20% glycerol, 20 mM 2-mercaptoethanol). The active protein and additionally also yellow accompanying substances were eluted at the next step of the gradient, 0.14 M KCl in standard buffer B (50 mM tris/HCl, pH 8.5, 20% glycerol, 20 mM 2-mercaptoethanol). The eluate obtained using 1 M KCl in standard buffer B (50 mM tris/HCl, pH 8.5, 20% glycerol, 20 mM 2-mercaptoethanol) was also yellow and contained ⅓ of the protein which had been loaded, but there was no acetyl transferase activity. With this last step, the column was simultaneously regenerated.

A great advantage of this purification step consists in the fact that the large volume of the AcA eluate is rapidly and gently concentrated to 4 ml (4 fractions of 1 ml each).

| Gradient: Time (min) | 1 M KCl in standard buffer B (%) |
|---|---|
| 0 | 0 |
| 35 | 0 |
| 35 | 7 |
| 45 | 7 |
| 45 | 14 |
| 55 | 14 |
| 55 | 100 |
| 70 | 100 |

[HighQ eluate: 4 ml, 8.8 mg of protein, 796 pcat]

This purification step achieved an enrichment factor of 121% compared to the AcA eluate, and removal of 66% of the foreign protein.

3.5 Hydroxyapatite

The column used was a CHT II column (from Biorad) which was filled with spherical hydroxyapatite $[Ca_5(PO_4)_3 OH]_2$ particles. In the presence of a low-molecular phosphate buffer, negatively charged proteins can be initially bound to the $Ca^{2+}$ cations and then displaced by higher phosphate concentrations in the elution buffer.

Basic proteins having a high pI have a relatively high affinity to the column material than those with a relatively low pI. The hydroxyapatite structure with $Ca^{2+}$ ions in the positively charged centres and $PO_4^{3-}$ in the negatively charged centres results in a mixed ion exchange separation. The HighQ eluate was pumped with a flow rate of 0.5 ml/min onto the CHT II column (5 ml) which had been equilibrated with phosphate buffer (10 mM $Na_2HPO_4$/ $NaH_2PO_4$, pH 6.8, 20% glycerol, 20 mM 2-mercaptoethanol), and the column was then washed with 12 ml of this buffer. The active protein was eluted at a concentration of 160 mM phosphate buffer (20% glycerol, 20 mM 2-mercaptoethanol). Even when the phosphate concentration was increased to 400 mM, no more protein could be eluted.

| Gradient: Time (min) | 160 mM phosphate buffer (%) |
|---|---|
| 0 | 0 |
| 40 | 0 |
| 40 | 100 |
| 70 | 100 |

The 0.5 ml fractions which had been collected were tested for protein and acetyl transferase activity.
[CHT II eluate: 1.5 ml, 0.73 mg of protein, 578 pcat]
This purification step achieved an enrichment factor of 8.7 compared with the HighQ eluate, combined with a removal of foreign protein of 92%, resulting in a loss of activity of 27%.

3.6 Dye Affinity Chromatography Over High Trap Blue

HiTrapBlue 1 ml (from Pharmacia) contains the synthetic polycyclic dye Cibacron Blue F3 G-A which is coupled to an agarose matrix. These ligands show a certain structural similarity to naturally occurring molecules such as the cofactors $NAD^+$ and $NADP^+$, which enables them to bind proteins strongly and specifically, inter alia enzymes which require adenylate-containing substances. The column material is therefore also referred to as "group-specific". However, the specificity is qualified by the fact that approximately a third of the enzymes which have hitherto been catalogued require a coenzyme containing a nucleotide component. Furthermore, it is also possible for proteins to bind unspecifically to the aromatic ligands owing to electrostatic and/or hydrophobic interactions.

Elution takes place specifically with the appropriate cofactor or unspecifically with salt solutions.

The acetyl transferase which binds the phosphoadenosyl diphosphate-containing acetyl CoA was absorbed to the blue column material and eluted unspecifically using a linear KCl gradient. For this purpose, the CHT II eluate was loaded in an FPLC unit (from Biorad) at a flow rate of 0.5 ml/min onto the High Trap Blue column which had been equilibrated with standard buffer B, and the column was washed with this buffer. The protein bound to the column was eluted at 0.5 ml/min using a linear salt gradient of 0–1 M KCl in standard buffer B (50 mM tris/HCl, pH 8.5, 20% glycerol, 20 mM 2-mercaptoethanol) over a period of 30 min.

| Gradient: Time (Min.) | 1 M KCl in standard buffer B (%) |
|---|---|
| 0 | 0 |
| 30 | 0 |
| 60 | 100 |

The fraction volume was 0.5 ml. Fractions containing activity were combined for further purification.
[High Trap Blue eluate: 1.5 ml, 0.05 mg of protein, 168 pcat]
Compared to the CHT II column, an enrichment factor of 4.2 was achieved in this purification step. A removal of 93% of foreign protein was associated with a total activity loss of 71%.

3.7 Hydrophobic Interaction Chromatography on Phenylsepharose

If certain neutral salts, such as, for example, $(NH_4)_2SO_4$ or KCl are added to proteins dissolved in an aqueous medium, the ionic strength of the solution is increased. Under these conditions, the hydrophobic regions on the surface of the proteins associate. In the same manner, they are also adsorbed onto column materials having hydrophobic ligands, and there are consequently hydrophobic interactions (HIC=Hydrophobic Interaction Chromatography). These interactions can subsequently be reduced again by using an elution buffer having a low salt concentration.

For this purification principle, it is therefore necessary to adjust the High Trap Blue eluate to a concentration of 0.5 M ammonium sulphate. This was achieved by adding the appropriate amount of ice-cooled 1 M ammonium sulphate solution in standard buffer B (50 mM tris/HCl, pH 8.5, 20% glycerol, 20 mM 2-mercaptoethanol) very slowly, a little at a time. The protein solution was subsequently loaded to the mini column (1 cm φ×1.3 cm) which had been equilibrated with 0.5 M $(NH_4)_2SO_4$ in standard buffer B. After the protein solution had penetrated the gel bed (phenylsepharose, from Pharmacia), the column was washed with 7 ml of 0.5 M $(NH_4)_2SO_4$ in standard buffer B (50 mM tris/HCl, pH 8.5, 20% glycerol, 20 mM 2-mercaptoethanol). In order to elute the bound protein, 0.1 M $(NH_4)_2SO_4$ in standard buffer B (50 mM tris, HCl, pH 8.5, 20% glycerol, 20 mM 2-mercaptoethanol) is used. The eluate is collected in fractions of 0.5 ml each and the relative protein concentration and the enzyme activity are determined. The most active fractions were combined and tested for activity and protein content. [Phenylsepharose eluate: 2.5 ml, 0.001 mg, 6.3 pcat] Compared to the HiTrapBlue eluate, the enrichment factor was calculated to be 1.9, with a simultaneous loss of activity of 96%, and 98% of the foreign protein being removed.

3.8 Dye Affinity Chromatography on Mimetic Green 1A-6 XL

As already discussed for the High Trap Blue column, there are also interactions between the cofactor binding site of an enzyme with the dye ligand of this material. Only the cofactor-dependent bound enzymes can then be eluted using the cofactor, in the present case acetyl coenzyme A. The unspecifically adsorbed proteins remain on the column.

Before the phenylsepharose eluate could be pipetted onto the Mimetic Green column (1 cm φ×1.2 cm, Affinity Chromatography Ltd., Freeport, Ballasalla, Isle of Man) it had to be desalted, and this in turn was carried out using a PD10 column (from Pharmacia). To this end, the 2.5 ml phenylsepharose eluate was applied to the PD 10 column and allowed to penetrate into it. Elution was carried out using standard buffer B (50 mM tris/HCl, pH 8.5, 20% glycerol, 20 mM 2-mercaptoethanol), the first 0.5 ml of eluate being discarded and the next 2.5 ml, which contained the active protein, being collected.

This enzyme solution was pipetted onto a Mimetic Green column (1 cm φ×1.2 cm) which had been washed with standard buffer B (50 mM tris/HCl, pH 8.5, 20% glycerol, 20 mM 2-mercaptoethanol). After the solution had penetrated the gel bed, it was eluted without a pump using successively the following solutions: 3 ml of standard buffer B (50 mM tris/HCl, pH 8.5, 20% glycerol, 20 mM 2-mercaptoethanol), 3 ml of 0.5 mM acetyl coenzyme A in standard buffer B, 2 ml of standard buffer B, 3 ml of 1 M KCl in standard buffer B. 1 ml fractions were collected and tested for protein and acetyl coenzyme A activity.

The acetyl coenzyme A eluate was the only fraction which contained acetyl transferase activity. Neither the initial flowthrough nor the KCl eluate contained any activity.

Prior to determining the activity in the acetyl CoA eluate, the cofactor had to be removed from the solution. The large pool of unlabelled acetyl coenzyme A would have diluted the small amount of $^{14}$C-labelled acetyl CoA to such an extent that virtually no radioactive substrate would have been converted.

The acetyl coenzyme A was removed almost completely using a PD 10 column as described above. The usual activity test was carried out on the eluate obtained in this manner. However, since the PD 10 eluate still contained traces of acetyl CoA from the elution buffer, i.e. it had not been possible to achieve complete removal, the pool of $^{14}$C-labelled CoA was diluted in the activity test, giving activity and purification factor values which were too low.

[Green eluate: 2.5 ml, 0.0001 mg of protein, 0.7 pcat]

In this purification step, the remaining foreign protein was removed, resulting in a purification factor of 1.1 at a loss of activity of 81%.

3.9 Summary of the Purification and Documentation of Homogeneity

Using the process described, the desired acetyl transferase was obtained from the crude extract by 70% strength ammonium sulphate precipitation and 8 column chromatography steps. This gave an acetyl transferase preparation whose specific activity was 280 times the value of the AcA eluate, the total yield being 0.1%. The great loss of activity during the purification, even though the AcA eluate was worked up in a single day, can be explained by the great instability of the enzyme and its sensitivity towards pH values below pH 8 and towards salt ions, in particular ammonium sulphate.

To check the purity of the enzyme preparation, denaturizing disc electrophoresis in the presence of SDS was used. Separation of the concentrated eluate of the mimetic green column using SDS-PAGE and subsequent silver staining revealed only 1 band.

| Purification step | Volume (ml) | Total activity (pcat) | Total protein (mg) | Specific activity (pcat/mg) | Yield (%) | Purification (x-fold) |
|---|---|---|---|---|---|---|
| Crude extract | 278 | — | 372 | — | — | — |
| $Ca_3(PO_4)_2$ | 285 | — | 194 | — | — | — |
| Sephadex G25 eluate | 82 | — | 78 | — | — | — |
| DEAE eluate | 110 | — | 59 | — | — | — |
| AcA 44 eluate | 53 | 724 | 25.7 | 28 | 100 | 1 |
| HighQ eluate | 4 | 796 | 8.8 | 90.5 | 121 | 3.2 |
| CHT II eluate | 1.5 | 578 | 0.73 | 792 | 80 | 43 |
| High Trap Blue eluate | 1.5 | 168 | 0.05 | 3360 | 23 | 120 |
| Phenylsepharose eluate | 2.5 | 6.3 | 0.001 | 6300 | 0.87 | 225 |
| Mimetic Green eluate | 2.5 | 0.7 | 0.0001 | 7000 | 0.1 | 280 |

EXAMPLE 4

Characterization of the Acetyl Transferase from *Taxus chinensis* Suspension Cultures 4.1 pH Optimum The pH has a great effect on the enzymatic activity since the charges of the functional groups of certain amino acids change depending on the acidity of the enzyme solution. This has implications on the conformation of the active centre of the enzyme and consequently on its activity. Likewise, the protonation pattern of certain substrates depends on the pH and can therefore also influence the enzyme activity.

To determine the optimum pH range, the transfer of acetyl coenzyme A to 10-deacetyltaxuyunnanin C was measured at various pH values from pH 5 to pH 11. For this purpose, 5.6 pcat (1.7 μg, 50 μl) of a 120-fold enriched acetyl transferase (High Trap Blue eluate) was used in the following mixtures:

Mixtures

50 μl 0.8 M tris, pH 8.5

50 μl acetyl transferase (5.6 pcat, 1.7 μg, 120-fold enriched)

30 μl acetyl coenzyme A (5 nmol, including 0.02 μCi[2-$^{14}$C]acetyl coenzyme A 5 μl 3 mM 10-deacetyltaxuyunnanin C (15 nmol)

50 μl of millipore water

Incubation 25 min at 35° C.

The mixtures were preincubated without acetyl coenzyme A for 5 minutes, and the reaction was then started by adding the cofactor. After an incubation time of 25 min at 35° C., the reaction was stopped by acidification and extraction with tert-butyl methyl ether. The radioactivity which was present in the ether extract was evaluated using a scintillation counter.

The acetyl transferase activity extended over the relatively narrow range of pH 8.5–9, the pH optimum being at pH 9. The half-maximum conversion rates are at pH 6.8 and pH 10.8.

Purification was carried out at pH 8.5 since in this case there was less active protein in the initial flowthrough of the affinity columns than at pH 9.

4.2 Optimum Temperature

In addition to the considerable influence that the pH has on the enzyme activity, the enzyme activity is also very dependent on the incubation temperature. The enzymatic activity initially increases with increasing temperature, but it then decreases rapidly from a certain temperature onwards, which is specific for each enzyme. At these high temperatures, denaturation and inactivation of the enzyme occur. To determine the optimum temperature of the acetyl transferase, 1.7 μg (5.6 pcat) of the 120-fold purified enzyme were incubated at temperatures of from 0° C. to 50° C., initially for 10 min without acetyl coenzyme A and then, after addition of the cofactor, for a further 25 min. The reaction was quenched by addition of 20 μl of 12% $H_2SO_4$. The taxuyunnanin C formed was then extracted using 600 μl of ether. The amount of product formed was then evaluated using a scintillation counter.

Mixtures

50 μl of 0.8 M tris, pH 8.5

50 μl of acetyl transferase (5.6 pcat, 1.7 μg, 120-fold enriched)

30 μl of acetyl coenzyme A (5 nmol, including 0.02 μCi[2-$^{14}$C]AcCoA

5 μl of 3 mM 10-deacetyltaxuyunnanin C (15 nmol)

50 μl of Millipore [lacuna]

Incubation 25 min at the respective temperature.

The optimum temperature for acetyl transferase is 35° C.

4.3 Isoelectric Point

The isoelectric point was determined by chromatofocussing. A specific anion exchanger, for example Mono P HR 5/20 (from Pharmacia), is used for this purpose, and the anion exchanger is loaded with the desired enzyme at a pH where it is present as an anion. Under these initial conditions, the enzyme binds to the column material and can then be eluted using an ampholyte-containing buffer mixture (Polybuffer 94, from Pharmacia) which forms a pH gradient through the column. The enzyme then detaches itself from the anion exchanger exactly at the point where the pH has been lowered to such an extent that the enzyme changes from the anionic to the formally uncharged state. This pH corresponds to the isoelectric point (IEP).

For the acetyl transferase, the IEP was determined using a BioLogic FPLC Workstation (from Biorad) with a Mono P HR 5/20 column (0.5 cm φ×20 cm, from Pharmacia) at a flow rate of 0.7 ml/min. This column was equilibrated using 25 mM imidazole/HCl pH 7.4 and loaded with HighQ eluate. To this end, 1 ml of HighQ eluate were concentrated to 100 μl using Centriprep concentrators (30 kD) and then diluted to 6 ml with the abovementioned imidazole buffer. Protein of this degree of purity was used here because the HighQ eluate contained the highest activity (pcat/ml) and chromatofocussing was anticipated to result in a high loss of activity. The column was washed with 10 ml of start buffer and the protein was eluted from the column using 40 ml of Polybuffer 74 (diluted 1:8 with Millipore water, pH 4). 1 ml fractions were collected, and to maintain the activity at low pH values, 100 μl of 0.8 M tris pH 8.5 were initially charged to every other fraction. The pH was measured in the intermediate fractions.

To determine the active fraction, an aliquot of every other fraction was incubated in the following mixture for 30 min:

Mixtures

200 μl of enzyme solution (buffered to pH 8.5)

30 μl of acetyl coenzyme A (5 nmol, containing 0.02 μCi[2-$^{14}$C]acetyl CoA)

5 μl of 3 mM 10 deacetyltaxuyunnanin C (15 nmol)

Incubation 30 min at 35° C.

Evaluation using a scintillation counter, after extraction with tert-butyl methyl ether.

The main activity eluted in the pH range from 5.7 to 5.47, so that the isoelectric point of the acetyl transferase was determined to be pH 5.6.

4.4 Determination of the Molecular Weight

To determine the molecular weight of the acetyl transferase, two different methods were employed: gel filtration using a calibrated gel filtration column and SDS gel electrophoresis.

The former was carried out using an FPLC unit (BioLogic Workstation, Biorad) at a flow rate of 0.2 ml/min and a Biosilect-SEC 250-5 column (Biorad) which had been equilibrated with 50 mM tris, pH 8.5, 10 mM 2-mercaptoethanol. First, the column was calibrated using proteins of a known molecular weight. Under identical conditions, 1.5 ml of High Trap Blue eluate which had been concentrated to 100 μl (3360 pcat, 50 μg of protein) using Centriprep concentrators (2 ml, membrane 10 kD), were then eluted through the column. The fraction size was 250 μl and the activity of the eluate was determined by incubation of the following mixtures (185 μl total volume):

Mixtures

50 μl of 0.8 M tris, pH 8.5

100 μl of eluate

30 μl of acetyl-CoA (5 nmol, which additionally contained 0.02 μCi[2-$^{14}$C]acetylCoA)

5 μl of 3 mM 10-deacetyltaxuyunnanin C (15 nmol)

Incubation 30 min at 35° C.

Evaluation was carried out using a scintillation counter, after extraction with tert-butyl methyl ether.

Using this method, a molecular weight of 72 kD was calculated for the acetyl transferase.

To check this value, the denaturing SDS gel electrophoresis was used. To this end, 0.3 μg of homogeneous protein were chromatographed in a 10% strength SDS gel in parallel with Marker proteins having a known molecular weight (Rainbow marker). The proteins were made visible by silver staining, so that the Rf values of the calibration proteins and the acetyl transferase could be compared, giving a molecular weight of 70.8 kD for the latter.

4.5 $K_M$ Value Determination

Determination of the $K_M$ Value for 10-deacetyltaxuyunnanin C

To gain information about the affinity of the acetyl transferase to 10-deacetyltaxuyunnanin C, the $K_M$ value of the phenylsepharose eluate was determined.

Mixtures

50 µl of 0.8 M tris, pH 8.5

100 µl of acetyl-transferase (0.25 pcat, 40 ng of protein, 225-fold enriched)

30 µl of acetyl coenzyme A (5 nmol, additionally containing 0.02 µCi[$2-^{14}C$]acetylCoA)

10 µl of 10-deacetyltaxuyunnanin C (final concen-tration: 0.1/0.3/1/3/5710/30/50/100/200/300/500 µM)

Incubation 30 min at 35° C.; evaluation of the radioactivity, which had been extracted using tert-butyl methyl ether, using a scintillation counter.

By plotting the measured results in a doubly reciprocal manner according to Lineweaver and Burk, the $K_M$ value for 10-deacetyltaxuyunnanin C was determined graphically to be 23 µM.

4.6 Determination of the $K_M$ Value for Acetyl Coenzyme A

The affinity of acetyl transferase to acetyl coenzyme A can be described by the $K_M$ value, which was determined using the phenylsepharose eluate.

Mixtures:

50 µl of 0.8 M tris, pH 8.5

100 µl of acetyl transferase (0.25 pcat, 40 ng of protein, 225-fold enriched)

30 µl of acetyl coenzyme A and $H_2O$ (final concentration 2.1/2.3/3/5/12/32/52/102/152/202/302/502 µM, each containing 2 µM (40,000 cpm) of [$2-^{14}C$]acetylCoA)

5 µl of 3 mM 10-deacetyltaxuyunnanin C (15 nmol)

Incubation 30 min at 35° C. Evaluation was subsequently carried out by extraction with tert-butyl methyl ether and the use of a scintillation counter. By plotting the measured values in a doubly reciprocal manner according to Lineweaver and Burk, the $K_M$ value for acetyl coenzyme A was determined at 61 µM.

4.7 Turnover Number $k_{cat}$

The turnover number describes the reaction rate of an enzymatic reaction by stating how many molecules of substrate are converted per second by one molecule of enzyme.

To determine the turnover, phenylsepharose eluate was used. The concentration of acetyl transferase contained therein was determined by separating the eluate using SDS-polyacrylamide gel electrophoresis, followed by silver staining. Known amounts of bovine serum albumin were applied as comparative concentrations to the adjacent slots of the gel.

Using 300 µl of enzyme solution corresponding to 18 ng of acetyl transferase, 10-deacetyltaxuyunnanin C and acetyl coenzyme A, the recorded turnover kinetic was linear in the range from 5 to 30 min.

Mixtures

50 µl of 0.8 M tris, pH 8.5

300 µl of acetyl transferase (18 ng of acetyl transferase, 0.76 pcat)

30 µl of acetyl coenzyme A (5 nmol, containing 0.02 µCi-[$2-^{14}C$] of acetylCoA)

5 µl of 3 mM 10-deacetyltaxuyunnanin C (15 nmol)

Incubation 30 min at 35° C.

The incubation mixtures were subsequently extracted with tert-butyl methyl ether and evaluated using the scintillation counter. The turnover (pmol) was calculated from the measured values. Division of the molecular weight (72 kD) by the amount of enzyme (18 ng) gives an enzyme concentration of 0.25 pmol per batch.

The enzyme activity is calculated by determining the turnover per unit of time (sec). The quotient of enzyme activity (0.05 pmol/sec) and concentration (0.25 pmol) gives a value of 0.2 cat/mol of homogeneous enzyme (mol/sec/mol of enzyme) for the turnover of the acetyl transferase.

Turnover=turnover no. $k_{cat}$: 0.05 pmol/sec: 0.25 µmol=0.2 cat/mol.

This corresponds to a turnover of 0.2 mol of substrate per second per mol (72 kg) of enzyme at 35° C., pH 8.5, and optimum amounts of substrate (60 mol of 10-deacetyltaxuyunnanin C, 20 mol of acetyl CoA).

4.8 Kinetic Optimum

Under physiological conditions, the concentration of substrate is very small compared to the concentration of enzyme. Only a small number of the active centres of the enzyme is occupied, so that the amount of enzyme which is not occupied by substrate [E] corresponds approximately to the total amount of enzyme [$E_0$].

If the concentration of substrate [S] is considerably below $K_M$, the concentration at which the initial reaction rate is half-maximal, the enzymatic reaction proceeds considerably more slowly than stated by the turnover number $k_{cat}$.

To characterize an enzyme under these conditions, the quotient $k_{cat}/K_M$ is used. If this value is multiplied by the substrate concentration [S] and the total amount of enzyme [$E_0$], the reaction rate is obtained.

$$v=(k_{cat}/k_m)[S][E_0]$$

It has to be taken into account that the rate of diffusion of molecules dissolved in an aqueous medium can be at most $10^8$ to $10^9$. Thus, the reaction rate is limited even for very fast enzymes, since it is not possible for the substrate to get to the enzyme more quickly.

The kinetic optimum calculated for the acetyl transferase is as follows:

$K_M$(10-deacetyltaxuyunnanin C)=23 µM, $k_{cat}$=0.2 cat/mol $k_{cat}/K_M$= 0.2 mol $s^{-1}$ $mol^{-1}$/23·$10^{-3}$[M]=8.7 $s^{-1}M^{-1}$

EXAMPLE 5

Substrate Specificity

To check the substrate specificity of the purified acetyl transferase, various compounds having a taxane skeleton were used as substrate.

10-deacetyltaxuyunnanin C
14-deacetyltaxuyunnanin C
10,14-deacetyltaxuyunnanin C
2,10,14-deacetyltaxuyunnanin C
5,10,14-deacetyltaxuyunnanin C
2,5,10,14-deacetyltaxuyunnanin C
2,14-deacetyltaxuyunnanin C
5,14-deacetyltaxuyunnanin C
2,5-deacetyl-10,14-deacetyltaxuyunnanin C
10-deacetylbaccatin III (=10-DAB III)
10-deacetyltaxol
10-deacetylcephalomannin
10-epi-10-DAB III
19-hydroxy-10-DAB III
14-hydroxy-10-DAB III

7-TES-10-DAB III
7-BOC-10-DAB III

It was found that, from among the substrates employed, only taxanes having a hydroxyl group in position C-10 can be converted. Taxane derivatives having an acetylated position C-10 but free hydroxyl groups at other carbons were not accepted as substrates by the purified acetyl transferase. However, if the access to C-10 is blocked by voluminous substituents, as in the case of 10-deacetyltaxol and 10-deacetylcephalomannin, acetylation does not take place.

When the rates of conversion were calculated, based on the rate of conversion of 10-deacetyltaxuyunnanin C, it was found that all taxuyunnanin C derivatives having a free hydroxyl group were converted to the same degree. 10-DAB is converted with a rate of conversion of 85%, compared to 10-deacetyltaxuyunnanin C to baccatin III.

The conversion of various substrates, based on the conversion of deacetyltaxuyunnanin C, is shown in the table below.

Conversion of Various Substrates, Based on the Conversion of 10-deacetyltaxuyunnanin C
10-deacetyltaxuyunnanin C
Enzyme: Phenylsepharose eluate (225-fold purified)

| Substrate | Conversion [%] | pkat |
|---|---|---|
| 10-Desacetyltaxuyunnanin C | 100 | 1.12 |
| 10-Desacetylbaccatin III | 80 | 0.9 |
| 10,14-Desacetyltaxuyunnanin C | 102 | 1.14 |
| 2,10,14-Desacetyltaxuyunnanin C | 81 | 0.91 |
| 5,10,14-Desacetyltaxuyunnanin C | 88 | 0.99 |
| 2,5,10,14-Desacetyltaxuyunnanin C | 53 | 0.59 |
| 10-epi-10-DAB III | 0 | 0 |
| 19-Hydroxy-10-DAB III | 38 | 0.43 |
| 14-Hydroxy-10-DAB III | 97 | 1.09 |
| 7-TES-10-DAB III | 0 | 0 |
| 7-BOC-10-DAB III | 2 | 2 |

What is claimed is:

1. A process for preparing baccatin or baccatin derivatives, comprising
    reacting 10-deacetylbaccatin or a 10-deacetylbaccatin derivative having an OH-group in position $C_{10}$ with an isolated enzyme and an effective amount of acetyl coenzyme A, the enzyme consisting essentially of an acetyl transferase having a molecular weight of from 70 to 72 kD determined by SDS-PAGE, with an isoelectric point of pH 5.6 and a Michaelis Menten constant $K_M$ for the acetyl coenzyme A of from 55 to 65 $\mu$M, wherein the acetyl transferase is obtained from *Taxus chinensis* cell cultures,
    to produce the baccatin or baccatin derivatives.

2. A process for preparing baccatin-III comprising
    reacting 10-deacetylbaccatin III with an isolated enzyme and acetyl coenzyme A, the enzyme consisting essentially of an acetyl transferase having a molecular weight of from 70 to 72 kD determined by SDS-PAGE, with an isoelectric point of pH 5.6 and a Michaelis Menten constant $K_M$ for the acetyl coenzyme A of from 55 to 65 $\mu$M, wherein the acetyl transferase is obtained from *Taxus chinensis* cell cultures,
    to produce baccatin-III.

3. A process for preparing 14-hydroxybaccatin-III comprising
    reacting 14-hydroxy-10-deacetylbaccatin-III with an isolated enzyme and acetyl coenzyme A, the enzyme consisting essentially of an acetyl transferase having a molecular weight of from 70 to 72 kD determined by SDS-PAGE, with an isoelectric point of pH 5.6 and a Michaelis Menten constant $K_M$ for the acetyl coenzyme A of from 55 to 65 $\mu$M, wherein the acetyl transferase is obtained from *Taxus chinensis* cell cultures,
    to produce 14-hydroxybaccatin-III.

4. A process for preparing taxuyunnanin C comprising
    reacting 10-deacetyltaxuyunnanin C with an isolated enzyme and acetyl coenzyme A, the enzyme consisting essentially of an acetyl transferase having a molecular weight of from 70 to 72 kD determined by SDS-PAGE, with an isoelectric point of pH 5.6 and a Michaelis Menten constant $K_M$ for the acetyl coenzyme A of from 55 to 65 $\mu$M, wherein the acetyl transferase is obtained from *Taxus chinensis* cell cultures,
    to produce taxuyunnanin C.

5. A purified enzyme obtained from *Taxus chinensis* cell cultures for selectively acetylating 10-deacetylbaccatin III at position 10 with an effective amount of acetyl coenzyme A, wherein the enzyme has:
    a) a molecular weight of from 70 to 72 kD determined by SDS-PAGE,
    b) an isoelectric point of pH 5.6,
    c) a Michaelis Menten constant $K_M$ for the acetyl coenzyme A of from 55 to 65 $\mu$M, and
    d) the enzyme is a 10-hydroxytaxa-O-acetyl transferase.

6. The enzyme according to claim 5, with a purity of >50%.

7. The enzyme according to claim 6, with a purity of >90%.

8. A process for identifying the presence of the enzyme according to claim 5, comprising
    a) providing a *Taxus chinensis* cell culture,
    b) performing a purification of the cell culture by precipitation, chromatography or a combination thereof, wherein a plurality of fractions are collected from the purification,
    c) adding deacetylbaccatin or a 10-deacetylbaccatin derivative and acetyl coenzyme A to the plurality of fractions, and
    d) detecting formation of an acetylation product to indicate the presence of the enzyme in one or more of the fractions of step c).

9. The process according to claim 8, wherein the purification step comprises contacting an anion exchange column with the enzyme-containing fractions.

10. The process according to claim 8, wherein the 10-deacetylbaccatin derivative is 10-deacetylbaccatin III or 10-deacetyltaxuyunnanin C.

11. The process according to claim 8, wherein the acetylation product is detected by radioactive labelling.

12. The process according to claim 8, wherein the acetylation product is detected by labelling with a heavy isotope.

13. A process for preparing taxol or taxol derivatives, comprising
    preparing the baccatin or baccatin derivatives according to claim 1,
    reacting the baccatin or baccatin derivatives with an acid to esterify the OH group at position 13 of the baccatin or baccatin derivatives to produce the taxol or taxol derivatives.

* * * * *